(12) United States Patent
Lombardi et al.

(10) Patent No.: US 7,424,322 B2
(45) Date of Patent: Sep. 9, 2008

(54) METHOD AND APPARATUS FOR STIMULUS ARTIFACT SUPPRESSION

(75) Inventors: Daniel J. Lombardi, Verona, WI (US); Steven Vos, Madison, WI (US)

(73) Assignee: Cardinal Health 209, Inc., Madison, WI (US)

( * ) Notice: Subject to any disclaimer, the term of this patent is extended or adjusted under 35 U.S.C. 154(b) by 382 days.

(21) Appl. No.: 11/050,464

(22) Filed: Feb. 3, 2005

(65) Prior Publication Data

US 2006/0173496 A1   Aug. 3, 2006

(51) Int. Cl.
*A61N 1/18* (2006.01)
(52) U.S. Cl. .............................. 607/2; 607/48; 600/554
(58) Field of Classification Search ................. 607/28, 607/48
See application file for complete search history.

(56) References Cited

U.S. PATENT DOCUMENTS

| | | | | |
|---|---|---|---|---|
| 3,641,993 | A | * | 2/1972 | Gaarder et al. .............. 600/546 |
| 4,722,343 | A | | 2/1988 | Lombardi |
| 4,811,742 | A | * | 3/1989 | Hassel et al. ................ 600/546 |
| 4,934,377 | A | | 6/1990 | Bova et al. |
| 5,143,081 | A | | 9/1992 | Young et al. |
| 5,758,651 | A | | 6/1998 | Nygard et al. |
| 5,851,191 | A | * | 12/1998 | Gozani ........................ 600/554 |
| 2003/0032889 | A1 | | 2/2003 | Wells |

OTHER PUBLICATIONS

International Search Report for PCT/US2006/003835 dated May 23, 2006.
Kevin C. McGill, et al., "On the Nature and Elimination of Stimulus Artifact in Nerve Signals Evoked and Recorded Using Surface Electrodes," IEEE Trans. On Biomed. Eng., vol. BME-29, No. 2, Feb. 1982, pp. 129-136.
Gehrke, Lombardi; Viking Select EMG 2 Channel Amplifier, Aug. 1, 2003; PCB Ref. 050-462102, sheet 3 of 10; Viasys Healthcare Neurocare Group, Madison WI.

* cited by examiner

*Primary Examiner*—Carl H. Layno
*Assistant Examiner*—Brian T Gedeon
(74) *Attorney, Agent, or Firm*—Baker & Hostetler LLP

(57) ABSTRACT

Amplification of an evoked potential signal is carried out utilizing a high pass filter implemented as an integrator in a feedback loop which drives the DC offset voltage to zero. As a result, the feed-forward amplifier circuit has almost zero volts at its output since the only voltage remaining is the offset voltage of the operational amplifier, which is selected so as to maintain this parameter as low as possible. Because the voltage impressed across the feed-forward amplifier section is close to zero, the gain of this section can be set to zero during the time that the electrical stimulus pulse is present without introducing any additional artifacts and subsequent amplifier stages are not driven into saturation. When the electrical stimulus potential is no longer present or is significantly reduced in amplitude and before the time of receipt of the response signal, the feed-forward amplifier is brought back into the circuit to provide the high gain required to amplify the response signal, which can be measured without interference from saturation of any of the amplifier stages as they recover to baseline.

18 Claims, 2 Drawing Sheets

METHOD AND APPARATUS FOR STIMULUS ARTIFACT SUPPRESSION

FIELD OF THE INVENTION

This invention relates generally to the field of evoked potential and nerve conduction testing and to instruments which apply electrical pulses to an individual to stimulate nerves and generate evoked potentials.

BACKGROUND OF THE INVENTION

Nerve conduction studies and evoked potential measurements are now commonly made in clinical practice and in research to evaluate nervous system functions. To measure the evoked potentials stimulated by electrical pulses, surface measurement electrodes are customarily positioned on the scalp or skin over peripheral nerves. The electrical potentials received by these electrodes are detected and analyzed by sensitive recording equipment. To stimulate a response in the nervous system, stimulation electrodes are applied to the skin of the subject at a position remote from the measurement electrodes, typically on an arm or leg, and a pulse of either constant voltage or constant current magnitude is then applied to the individual between the two stimulation electrodes.

In performing sensory nerve conduction studies, it is necessary to use relatively high levels of voltage (e.g., hundreds of volts) and/or current (e.g., tens of milliamperes) to depolarize the nerve and elicit a response. Once the nerve is depolarized, the compound nerve action potential (CNAP) travels along the nerve in both directions. The velocity of this response is an important parameter in the diagnosis of various neuropathies.

To determine the velocity of this CNAP, recording electrodes are placed directly over the nerve being stimulated. By connecting these recording electrodes to a physiological amplifier, both the amplitude and the latency (the time it takes for the response to reach the recording electrodes) can be determined. Where neuropathies are present, the amplitudes can be less than a microvolt. In addition, for short nerve conduction distances, the latencies can be on the order of one to two milliseconds. The nerve conduction velocity is calculated by taking the ratio of the distance of conduction to the latency time.

A significant difficulty is encountered in measuring the response potentials because the electrical stimulator produces a large electric field potential. This field potential reaches the recording electrodes almost instantly and generates a response commonly referred to as the "stimulus artifact." This artifact is problematic for two reasons. First, since the response potential is so small, the amplifier gains are typically set very high. Therefore, the large potential from the stimulator drives various stages of the amplifier into saturation. As a result, the amplifier may still be recovering from the saturation condition and have not returned to baseline when the response potential arrives. This can obscure the "take-off" point of the response and introduce an error in the velocity calculation. Secondly, the physiological amplifier is usually AC coupled through a high pass filter capacitor so that DC offset potentials on the electrodes can be removed from the signal picked up by the electrodes. However, the large potential from the stimulus artifact can inject a charge on this filter capacitor, and the resulting RC time constant can, again, create a delay in the return of the amplifier to baseline.

SUMMARY OF THE INVENTION

In accordance with the present invention, amplification of the evoked potential signal is carried out utilizing a high pass filter implemented as an integrator in a feedback loop which drives the DC offset voltage to zero. As a result, the feed-forward amplifier circuit has almost zero volts at its output since the only voltage remaining is the offset voltage of the operational amplifier, which is selected so as to maintain this parameter as low as possible. Because the voltage impressed across the feed-forward amplifier section is close to zero, the gain of this section can be set to zero during the time that the electrical stimulus pulse is present without introducing any additional artifacts. As a consequence, subsequent amplifier stages are not driven into saturation during the time that the electrical stimulus artifact is present, the electrical stimulus potential cannot inject a significant amount of charge onto the high pass filter capacitor, and during a time interval following initiation of the stimulus in which the feed-forward section gain is set to zero, a reference base line can be established at the beginning of the data record. When the electrical stimulus potential is no longer present or is significantly reduced in amplitude and before the time of receipt of the response signal (CNAP pulse), the feed-forward amplifier is brought back into the circuit to provide the high gain required to amplify the CNAP signal, which can now be measured without interference from saturation of any of the amplifier stages causing prolonged baseline recovery.

The evoked potential amplifying apparatus of the invention receives the evoked potential signal from the sensing electrodes and a stimulus signal from a stimulator that indicates when a stimulus pulse is applied. The amplifying apparatus includes a first or feed-forward amplifying section having an input receiving a signal from the evoked potential electrodes and providing an amplified output signal, and a second amplifier section receiving the output of the first or feed-forward amplifying section and providing an output signal, the first and second amplifying sections connected in a feedback circuit to provide high gain amplification of the evoked potential signal. A coupling capacitor is connected in a feedback loop to the input of the second amplifier section to configure the second amplifier section as an integrator. This configuration allows the evoked potential signal to pass through while blocking DC components. A controllable switch is connected across the first amplifier section from its inverting input to its output. The controllable switch receives a switch control signal indicating the application of a stimulus pulse to close the controllable switch and 'short out' the first amplifier section during the stimulus signal and, preferably for a selected period of time following the stimulus signal, reducing the overall gain of the amplifying apparatus. The controllable switch is opened after the selected period of time to thereafter provide high gain amplification to the evoked potential signal. A delay circuit is preferably connected to the control input of the controllable switch to provide a control signal to the switch to hold the switch closed for a selected period of time after the stimulus pulse has ended. The amount of the time delay can be selected to provide an appropriate reduction of the effect of stimulus artifact while providing full amplifier operation at the time of arrival of the evoked signal. The delay may be a fixed value from zero to a few hundred microseconds, or it may be adjustable and dependent on the duration of the stimulus pulse.

The first amplifier section may be implemented as an operational amplifier with inverting and non-inverting inputs and configured to provide high gain through the section. A low pass input filter may also be utilized to reduce the effect of high frequency noise on the input signal in a conventional manner.

Further objects, features and advantages of the invention will be apparent from the following detailed description when taken in conjunction with the accompanying drawings.

DETAILED DESCRIPTION OF THE INVENTION

Figure 1:
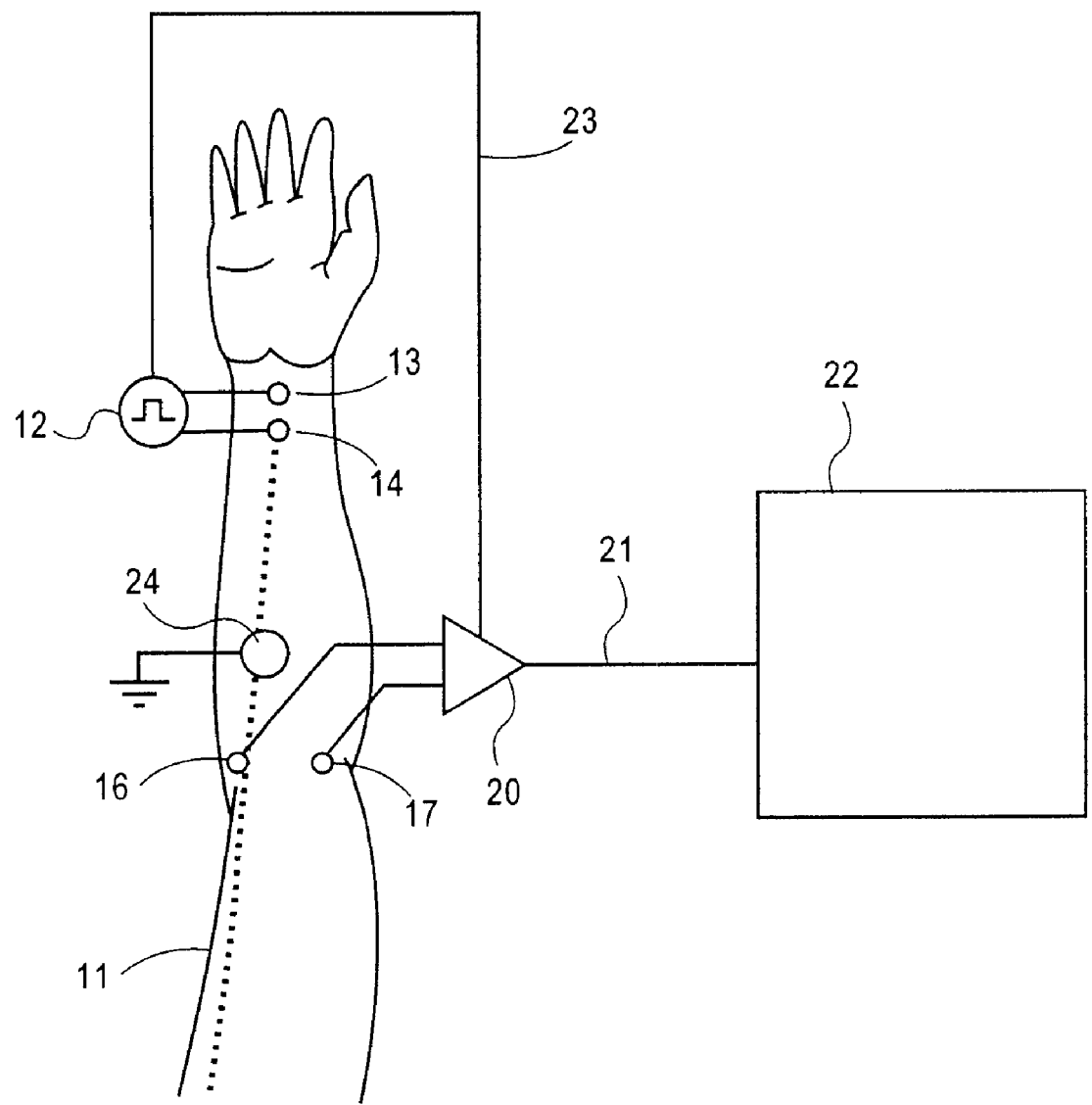
FIG. 1 is a simplified view illustrating the application of the apparatus of the invention to an individual for nerve conduction testing.

A pictorial view illustrating a typical application of evoked potential stimulation apparatus is shown in FIG. 1 to provide an example of the invention, arranged for measuring the response of the median nerve in a subject's arm 11. The electrical stimulus is provided from a stimulator 12 to anode and cathode stimulation electrodes 13 and 14, respectively. An example of stimulation apparatus for applying electrical stimulus pulses to a subject is described in U.S. Pat. No. 4,722,343, issued Feb. 2, 1988, the disclosure of which is incorporated herein by reference. The nerve response signal is recorded at sensing electrodes 16 and 17 which are connected to and the signals from which are received by a recording amplifier 20 in accordance with the invention, which provides its amplified output signal on a line 21 to an analyzer 22. The stimulus pulse from the stimulator 12 is supplied via a connecting line 23 to the recording amplifier 20 for use in accordance with the invention, as described further below. The subject's arm is connected to a recording amplifier common by an electrode 24 positioned between the stimulus electrodes and the sensing electrodes to reduce 60-Hz interference, to hold the mean voltage of the arm near ground, and to prevent transthorasic current flow if a failure shorts one of the stimulator leads to supply voltage or ground. The application of the stimulus pulse from the stimulator 12 creates a large stimulus artifact that is picked up by the sensing electrodes 16 and 17. The nature of the stimulus artifact is described in the paper by Kevin C. McGill, et al., "On the Nature and Elimination of Stimulus Artifact in Nerve Signals Evoked and Recorded Using Surface Electrodes," IEEE Transactions on Biomedical Engineering, Vol. BME-29, No. 2, February, 1982, pp. 129-136.

Figure 2:
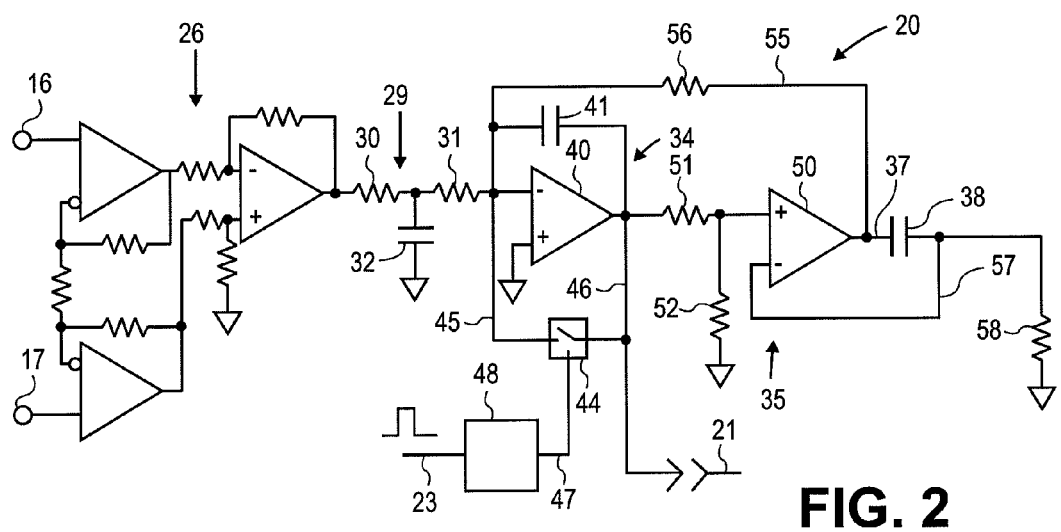
FIG. 2 is a schematic circuit diagram of the evoked potential amplification apparatus in accordance with the invention.

A schematic circuit diagram of a preferred implementation of the amplifying apparatus 20 in accordance with the present invention is shown in FIG. 2. The input signals from the electrodes 16 and 17 are amplified by a differential preamplifier 26 having relatively low gain (e.g., ×10) and which is not subject to saturation during the stimulus pulse. The evoked response signal picked up by the electrodes 16 and 17 is provided to an optional low pass filter 29, composed of series resistors 30 and 31 and a parallel capacitor 32, which may be utilized as appropriate to restrict high frequency noise, e.g., thermal or environmental noise. The amplifying apparatus 20 includes a first, or feed-forward, amplifying section 34 which receives a signal passed through the low pass filter 29, and a second amplifying section 35 that receives a signal from the first section 34 and provides an amplified output signal on a line 37 that has been passed through an integrator using a coupling capacitor 38. The coupling capacitor 38 functions as a high pass filter to restrict low frequency noise and to provide DC blockage. The evoked potential signal is provided on the output line 21 to an analyzer 22.

The first amplifying section 34 has a high gain operational amplifier 40, with a feedback capacitor 41 connected back to the inverting input of the operational amplifier 40. A controllable switch 44 is connected by lines 45 and 46 across the amplifying section 34 and receives a control signal on a control line 47 from a hold and delay circuit 48 that receives the stimulus pulse from the line 23. The controllable switch 44 may be any bidirectional switching element having appropriate controllable on and off response times and low "on" resistance. Where mechanical relays have adequate response times, they may be utilized while, generally, bi-directional semiconductor switches having fast on and off times in response to the control signal provided to the switch are preferred. When the stimulus pulse is received on the line 23, the hold and delay circuit 48 provides an output pulse on the line 47 to close the switch 44 at initial receipt of the stimulus pulse and for at least the duration of the stimulus pulse. The on-time of the signal provided on the line 47 to close the switch 44 may be selected as discussed below, and is never less than the stimulus pulse duration and can be extended, if appropriate, during a delay time in the range of a few microseconds to 600 microseconds after the stimulus pulse. When the switch 44 is closed, the first amplifying section 34 has its gain reduced to nearly zero and can be modeled as an equivalent voltage source supplying the amplifier offset voltage $V_{OS}$ as shown in FIG. 3.

The second amplifying section 35 includes an operational amplifier 50 which receives the output of the amplifying section 34 through a voltage divider composed of resistors 51 and 52 to its non-inverting input. The output of the operational amplifier 50 is fed back via a line 55 through a feedback resistor 56 to the inverting input of the amplifier 40 to provide a selected high gain through the two amplifying sections 34 and 35 when the first amplifying section 34 is still in the high gain configuration. The signal passed through the coupling capacitor 38 is passed back on a line 57 to the inverting input of the operational amplifier 50, so that the second amplifying section 35 is essentially an integrator in which the capacitor 38 is in the feedback loop. Because the coupling capacitor 38 is in the feedback loop of the amplifying section 35, any DC offset voltage appearing at the input of the integrator will be driven back to zero. During the time that the switch 44 is closed, the time constant of the high pass filter (the corner frequency of which is determined by the values of the integrator capacitor 38 and a resistor 58 connected from the capacitor to common) is effectively increased by a factor inversely proportional to the very low gain established at that time. This has the added advantage of reducing the amount of charge transferred to the coupling capacitor 38 by any small amount of residual voltage present due to either the stimulus voltage or the amplifier offset voltage $V_{OS}$.

Figure 3:
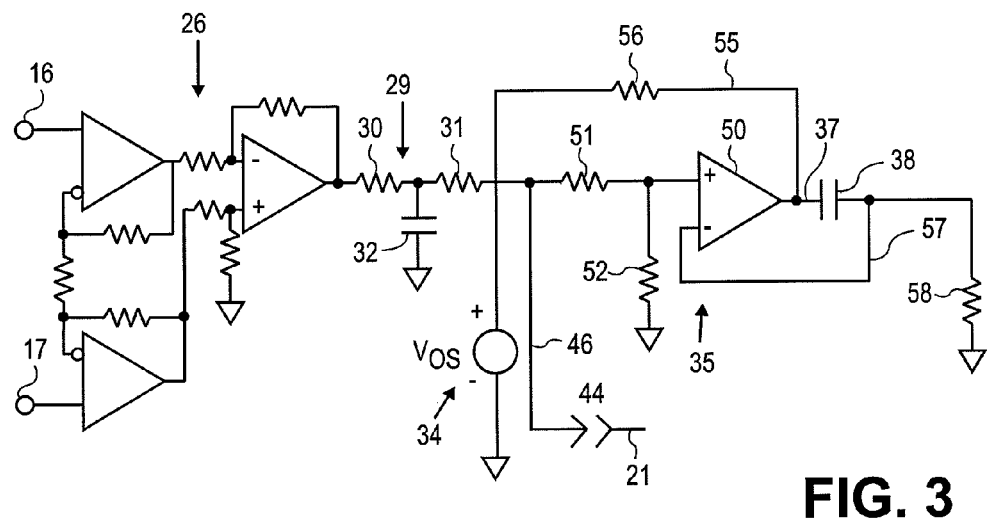
FIG. 3 is a schematic circuit diagram of the equivalent circuit configuration for the circuit of FIG. 2 during a time after application of a stimulus pulse in which the first amplifier section is effectively shorted to reduce the amplification of the circuit.

After application of a stimulus pulse, the hold and delay circuit 48 provides a control signal on the line 47 to the switch 44 to close the switch and essentially reduce the gain of the first amplifying section 34 to nearly zero, to provide the equivalent circuit shown schematically in FIG. 3 during the delay time from the hold and delay circuit 48. During the time of the delay provided from the hold and delay circuit 48, the amplifying section 34 provides very low gain amplification (preferably, essentially zero gain) for the input signal received from the electrodes 16 and 17 and, consequently, the relatively large electrical pulse corresponding to the stimulus pulse that is picked up by the electrodes 16 and 17 does not saturate successive amplifier stages. Furthermore, the action of closing the switch 44 does not create an additional artifact because the integrator has driven any DC voltage across it to zero. After the period of delay provided by the hold and delay circuit 48, the switch 44 is again opened so that the high gain of the first amplifying section 34 is restored. The time of the delay provided by the hold and delay circuit 48 is selected so that it effectively suppresses the large stimulus artifact signal, but the delay is terminated before the expected time of arrival of the evoked potential response waveform and at a time sufficiently before the arrival of the response waveform so that the operational amplifiers have stabilized. Because the stimulus artifact generally will have substantially subsided before the first amplifier section 34 is connected back into the circuit, the amplifiers will not be subject to saturation and will not require a long recovery time before they are ready to receive and accurately amplify the evoked potential response.

It is understood that the invention is not confined to the particular embodiments set forth herein as illustrative, but embraces all such forms thereof as come within the scope of the following claims.

What is claimed is:

1. Evoked potential amplifying apparatus adapted to receive an evoked potential signal from sensing electrodes and a stimulus signal from a stimulator indicating when a stimulus pulse is applied, comprising:
   a first amplifier section having an input for receiving a signal from the evoked potential sensing electrodes and providing an amplified output;
   a second amplifier section receiving the output of the first amplifier section and providing an output signal, the output from the second amplifier section connected by a feedback loop to an input of the first amplifier section;
   a coupling capacitor connected to receive the output of the first amplifier section and connected in a feedback loop to an input of the second amplifier section;
   a controllable switch connected across the first amplifier section and receiving a switch control signal indicative of application of the stimulus pulse, the controllable switch closing when receiving the control signal to reduce the gain of the first amplifier section to nearly zero and thereby to reduce the overall gain of the amplifying apparatus; and
   a hold and delay circuit connected to the controllable switch to apply a control signal thereto and adapted to receive the stimulus signal from the stimulator.

2. The amplifying apparatus of claim 1, further comprised of the hold and delay circuit providing a control signal to the controllable switch to hold the switch closed for a selected period of time after the end of the stimulus signal and thereafter controlling the controllable switch to open such that the amplifying apparatus provides high gain thereafter to the evoked response signal.

3. The amplifying apparatus of claim 2 wherein the selected time delay provided by the hold and delay circuit after the end of the stimulus signal is in the range of a few microseconds to 600 microseconds.

4. The amplifying apparatus of claim 1 wherein the first amplifier section includes an operational amplifier with inverting and non-inverting inputs and a capacitor connected in a feedback loop from the output of the operational amplifier to the inverting input.

5. The amplifying apparatus of claim 1 further including a low pass input filter connected to the first amplifier section to provide a low pass filtered evoked potential signal thereto.

6. The amplifying apparatus of claim 5 further comprising a pulse stimulator providing a stimulus signal and connected to the amplifying apparatus to provide the stimulus signal thereto.

7. The amplifying apparatus of claim 1 further comprising a differential preamplifier receiving the signals from the sensing electrodes and providing an output signal for transmission to the first amplifier section.

8. A method of amplifying evoked potential signals from sensing electrodes during an evoked potential test, comprising:
   providing an electrical stimulus pulse to a subject to stimulate an evoked potential from a nerve or nerves in the subject;
   receiving the evoked potential signal from sensing electrodes attached to the subject;
   providing the signal from the sensing electrodes to a first amplifier having a low gain at least during the stimulus pulse, and passing the output of the first amplifier through a coupling capacitor to provide a DC filtered output signal, the signal passed through the capacitor connected in a feedback loop to the amplifier such that the DC voltage across the first amplifier is reduced toward zero, and maintaining the low gain of the first amplifier for a selected period of time after initiation of the stimulus pulse; and
   thereafter providing high gain amplification from the first amplifier to amplify the signal from the sensing electrodes with a selected high gain beginning at a time prior to an expected time of arrival of an evoked potential signal received at the sensing electrodes, with the low gain of the first amplifier being maintained for a selected period of time after the stimulus pulse has ended.

9. The method of claim 8 further comprising low pass filtering the signal received from the sensing electrodes before amplifying the signal.

10. An evoked potential amplifying apparatus, comprising:
    a first amplifier section having an input for receiving a signal from an evoked potential sensing electrodes and providing an amplified output;
    a second amplifier section receiving the output of the first amplifier section and providing an output signal, the output from the second amplifier section connected by a feedback loop to an input of the first amplifier section;
    a first unit restricting low frequency noise and blocking direct current, the first unit connected to receive the output of the first amplifier section and connected in a feedback loop to an input of the second amplifier section;
    a controllable switch connected across the first amplifier section and receiving a switch control signal indicative of application of a stimulus pulse from a stimulator indicating when a stimulus pulse is applied, the controllable switch closing when receiving the control signal to reduce the gain of the first amplifier section to nearly zero and thereby to reduce the overall gain of the amplifying apparatus; and
    a hold and delay circuit connected to the controllable switch providing a control signal to the controllable switch to hold the switch closed for a selected period of time after the end of the stimulus signal and thereafter controlling the controllable switch to open.

11. The amplifying apparatus of claim 10, wherein the first amplifier has a low gain that is maintained for a selected period of time after the stimulus pulse has ended.

12. The amplifying apparatus of claim 11, wherein the first unit is a coupling capacitor.

13. The amplifying apparatus of claim 10, further comprised of the hold and delay circuit providing a control signal to the controllable switch to hold the switch closed for a selected period of time after the end of the stimulus signal and thereafter controlling the controllable switch to open such that the amplifying apparatus provides high gain thereafter to the evoked response signal.

14. The amplifying apparatus of claim 10, further comprised of the hold and delay circuit connected to the controllable switch providing a control signal to the controllable switch to hold the switch closed for a selected period of time after the end of the stimulus signal and thereafter controlling the controllable switch to open, where the amplifying apparatus provides high gain thereafter to the evoked response signal.

15. The amplifying apparatus of claim 10, wherein the selected time delay provided by the hold and delay circuit after the end of the stimulus signal is not more than 600 microseconds.

16. The amplifying apparatus of claim 12, wherein the first amplifier section comprises an operational amplifier with inverting and non-inverting inputs and a capacitor connected in a feedback loop from the output of the operational amplifier to the inverting input.

17. The amplifying apparatus of claim 12, further comprising a low pass input filter connected to the first amplifier section to provide a low pass filtered evoked potential signal thereto.

18. The amplifying apparatus of claim 12, further comprising a pulse stimulator providing a stimulus signal and connected to the amplifying apparatus to provide the stimulus signal thereto.

* * * * *